United States Patent [19]

Nicolau et al.

[11] Patent Number: 5,691,267

[45] Date of Patent: Nov. 25, 1997

[54] TWO STEP GOLD ADDITION METHOD FOR PREPARING A VINYL ACETATE CATALYST

[75] Inventors: Ioan Nicolau; Azael T. Flores, both of Corpus Christi, Tex.

[73] Assignee: Hoechst Celanese Corporation, Somerville, N.J.

[21] Appl. No.: 696,413

[22] Filed: Aug. 13, 1996

Related U.S. Application Data

[63] Continuation-in-part of Ser. No. 633,275, Apr. 16, 1996, abandoned.

[51] Int. Cl.$^6$ ........................................... B01J 23/52
[52] U.S. Cl. ..................... 502/330; 502/333; 502/344; 502/339
[58] Field of Search ........................... 502/330, 333, 502/344, 339

[56] References Cited

U.S. PATENT DOCUMENTS 4,087,622   5/1978   Nakamura et al. ................. 560/245
5,314,858   5/1994   Colling et al. ..................... 502/330
5,332,710   7/1994   Nicolau et al. .................... 502/243
5,422,329   6/1995   Wirtz et al. ....................... 502/328

Primary Examiner—Glenn Caldarola
Assistant Examiner—Nadine Preisch
Attorney, Agent, or Firm—Donald R. Cassady; M. Susan Spiering

[57] ABSTRACT

A method for preparing a catalyst wherein a catalytic carrier is impregnated with water-soluble palladium and gold compounds followed by fixing and then reducing the fixed palladium and gold compounds to palladium and gold metal followed by impregnating the carrier with a second amount of a water-soluble gold compound. The second amount of gold compound is fixed then reduced to gold metal. The catalyst then is impregnated with an alkali metal acetate such as potassium acetate. The catalyst can be employed to synthesize unsaturated esters such as vinyl acetate.

29 Claims, No Drawings

TWO STEP GOLD ADDITION METHOD FOR PREPARING A VINYL ACETATE CATALYST

RELATIONSHIP TO PRIOR APPLICATIONS

This application is a continuation-in-part to application Ser. No. 08/633,275, filed Apr. 16, 1996—now abandoned.

BACKGROUND OF THE INVENTION

The present invention relates to a novel method of making a catalyst useful for synthesizing unsaturated esters by gas phase reaction. In particular, the present invention is directed to a novel method of making a catalyst useful in the gas phase formation of vinyl acetate from the reaction of ethylene, oxygen and acetic acid.

It is known in the art to produce vinyl acetate by reacting ethylene, oxygen and acetic acid in a gaseous phase and in the presence of a catalyst comprising palladium, gold and an alkali metal acetate supported on certain carrier materials such as silica. Such catalyst systems exhibit a high activity. Unfortunately, results utilizing such palladium and gold catalysts have been inconsistent. This inconsistency appears to be based somewhat on the distribution pattern or profile of the catalyst components which are deposited on and in relation to the carrier. For example, when use is made of the known vinyl acetate catalyst systems comprising a porous support with palladium and gold, the metal components deposited at or about the carrier interiors or central regions do not contribute significantly to the reaction mechanism, since the reactants are not readily able to diffuse into the central or inner regions of the porous network of the catalyst. More importantly, products of catalyst synthesis formed in the catalyst interior must diffuse from the interior outward, again coming in contact with the active phase in the outer region of the catalyst. Consequently, these interior-formed products undergo further reaction and are often converted to unuseful by-products. The most effective reactions occur when the catalytic metal is formed as a thin shell impregnated within the surface regions of the catalyst as diffusion of reactants and products can be readily achieved to provide good product yields and reduced by-product formulation.

Various patents have been granted based on the desire to more evenly distribute and anchor the gold and palladium catalytic components within a narrow band on the carrier surface to provide a vinyl acetate catalyst having high yield, good selectivity and long life. Examples of such patents include U.S. Pat. Nos. 4,087,622; 4,048,096; 3,822,308; 3,775,342 and British Patent 1,521,652.

The basic method of forming a vinyl acetate catalyst containing palladium and gold deposited on a catalyst carrier comprises (1) impregnating the carrier with aqueous solutions of water-soluble palladium and gold compounds, (2) precipitating the water-insoluble palladium and gold compounds on the catalyst carrier by contacting the impregnated catalyst carrier with a solution of compounds capable of reacting with the water-soluble palladium and gold compounds to form the water-insoluble precious metal compounds (3) washing the treated catalyst with water to remove anions which are freed from the initially impregnated palladium and gold compounds during precipitation and (4) converting the water-insoluble palladium and gold compounds to the free metal by treatment with a reducing agent. A final treatment usually involves (5) impregnating the reduced catalyst with an aqueous alkali metal acetate solution and (6) drying the final catalyst product.

Attempts to provide a uniform distribution of the palladium and gold metals on the carrier has involved manipulation of the above mentioned steps and/or by using carrier materials having various specified pore dimensions. Particularly useful improvements in preparing highly active catalysts for preparing vinyl acetate are described in commonly assigned U.S. Pat. Nos. 5,314,858 and 5,332,710 both of which are herein incorporated by reference. These two patents describe processes for improving palladium and gold distribution on a carrier by manipulating precipitation step (2), the "fixing" of the water soluble precious metal compounds to the carrier as water-insoluble compounds. In U.S. Pat. No. 5,314,858, fixing precious metals on the carrier is achieved utilizing two separate precipitation stages to avoid using large excesses of "fixing" compound. U.S. Pat. No. 5,332,710 describes fixing the precious metals by rotating impregnated catalyst carriers while the impregnated carriers are immersed in a reaction solution at least during the initial precipitation period. Such roto-immersion procedure has been found to yield catalysts in which the precipitated carrier metals are more evenly distributed in a narrow band on the carrier surface.

Attempts to improve catalytic activity, usually evaluated by the space time yield (STY), have involved using catalyst carriers of particular pore size or particular shapes. Catalyst carriers useful for producing vinyl esters are typically composed of silica, alumina, aluminum silicates or spinels. Silica is the preferred carrier material because silica is porous and is a neutral carrier for precious metal deposition. The carriers usually shaped as spheres, tablets or cylinders in the range of 4–8 mm are often employed. As the catalytic activity increases it is preferable for the purpose of producing an unsaturated ester on an industrial scale, to increase the raw material gas volume comprised of olefin, organic carboxylic acid and oxygen passing across the catalyst. Catalyst shape and porosity affect gas volume flow across the catalyst. One reason to increase raw material gas volume passing across a catalyst is to prevent formation of hot spots on the active catalyst. Since formation reactions of unsaturated esters are exothermic, an increase in catalytic activity can excessively heat portions of the catalyst. Inefficient heat distribution on a catalyst leads to side reactions such as the formation of carbon dioxide which results in less selectivity for the formation of the unsaturated ester such as vinyl acetate.

Another problem associated with increasing activity of the vinyl ester catalysts is the production of heavy ends during vinyl ester synthesis. Heavy ends are by-product residues which comprise high molecular weight organic compounds formed during unsaturated ester synthesis. Such heavy ends include, but are not limited to, ethylidene diacetate; 1,1-diacetoxy ethylene; cis and trans-diacetoxy ethylene; ethylene glycol diacetate; vinyl acetoxyacetate; vinyl acetoxyacetic acid; ethylene glycol monoacetate; and cyclopropane carboxylic acid. Unsaturated ester synthesis, such as vinyl acetate synthesis, can often produce a heavy ends selectivity of up to about 2% based on the reactant ethylene. The heavy ends can be readily removed and separated from the desired product by distillation, and the bottoms containing the heavy ends collected and disposed of by waste site dumping or burning. However, disposal of the heavy ends are considered toxic or the burning thereof can cause formation and release of toxic products into the environment. Pollution laws and guidelines in many areas of the world strictly limit the ability to dump toxic solid waste or to burn same. Thus, any reduction in heavy ends formation during unsaturated ester synthesis is very desirable.

Catalytic acitivity of the vinyl ester synthesis catalyst has been improved by increasing the relative mount of gold added to the support. It has now been found that increased gold content of the vinyl ester synthesis catalyst maintains the life of the catalyst and lowers both $CO_2$ selectivity and heavy ends.

Although there are catalysts and methods for preparing catalysts with an improved uniform distribution of palladium and gold metals on a catalyst carrier and high catalyst activity, there is still a need for a method of preparing vinyl acetate catalysts having a more uniform distribution of palladium and gold on the carrier surface and particularly, for increasing the gold content of the catalyst. Present methods of adding gold to the catalyst do not necessarily insure a desired gold content in the finished catalyst due to substantial leaching or abrasion of the gold, or gold salts from the catalyst during preparation.

Accordingly, it is an object of the present invention to provide for a method of preparing a vinyl ester catalyst which has an increased amount of gold metal.

Another object of the present invention is to provide a method of preparing a vinyl ester catalyst having an improved selectivity for vinyl ester such as vinyl acetate.

A further object of the present invention is to provide a method of preparing a vinyl acetate catalyst having reduced selectivity for carbon dioxide and ethyl acetate. An additional object of the .present invention is-to provide a vinyl ester catalyst having a high catalyst activity.

Other objects and advantages of the present invention are set forth in the description which follows and will become apparent to a person of skill in the art upon practicing the present invention.

SUMMARY OF THE INVENTION

It has now been found that highly active supported catalysts containing palladium and gold useful for the production of vinyl esters from ethylene, lower carboxylic acids with 2–4 carbon atoms and oxygen in the gas phase at elevated temperature and at normal or elevated pressure can be obtained by adding gold to the catalyst carrier in two steps. Typically, the gold component of the vinyl ester catalyst has been added to the catalyst carriers in a single impregnation step and fixed thereon. For example, the gold is impregnated onto the catalytic carrier as a solution of a water-soluble salt or acid simultaneously with a water-soluble salt of palladium metal, or alternatively, the gold is added in a step separate from palladium addition. The impregnated water-soluble palladium and gold compounds are then fixed by forming water-insoluble palladium and gold compounds with an alkaline fixing solution and the water-insoluble palladium and gold compounds then reduced to palladium and gold metal. Unfortunately, as discussed above, addition of gold to a catalyst carrier in a single step often results in loss of gold from the surface of the carrier through leaching or abrasion during catalyst preparation. Thus, high catalyst activity and high vinyl acetate selectivity can not always be expected.

To overcome such problems and in accordance with the present invention, an improved vinyl ester catalyst is formed by (1) simultaneously or successively impregnating a catalyst carrier with aqueous solutions of a water-soluble palladium salt and a first amount of a water-soluble gold compound such as sodium-palladium chloride and auric chloride, (2) fixing the precious metals on the carrier by precipitating the water-insoluble palladium and gold compounds by treatment of the impregnated carriers with a reactive basic solution such as aqueous sodium hydroxide which reacts with the palladium and gold compounds to form hydroxides of palladium and gold on the carrier surface, (3) washing with water to remove the chloride ion (or other anion), and (4) reducing all the precious metal hydroxides to free palladium and gold, wherein the improvement comprises (5) impregnating the carrier with a second amount of a water-soluble gold compound subsequent to fixing a first amount of water-soluble gold agent, and (6) fixing the second amount of a water-soluble gold compound. The first and second amounts of gold can be reduced either after each of the respective fixing steps, or all the gold can be reduced in a final reduction step after the separate fixing of the first and second amounts of gold. What has been found is that catalyst activity with respect to the formation of vinyl esters such as vinyl acetate by the process of reacting ethylene, lower carboxylic acid and oxygen in the gas phase can be maintained and that the side reaction relative to the formation of carbon dioxide is substantially reduced when the catalysts are formed by the method described.

DETAILED DESCRIPTION OF THE INVENTION

In an improved method of preparing a catalyst employed in the synthesis of unsaturated esters, gold is added to a catalyst carrier in two separate steps.

The carrier material for the catalyst according to the present invention can be of any diverse geometrical shape. For example, the carrier can be shaped as spheres, tablets or cylinders. The geometrical dimensions of the carrier material can, in general, be in the range of about 1–8 mm. A most suitable geometrical shape is, in particular, the spherical shape, for example, spheres with diameters in the range of about 4–8 mm.

The specific surface area of the carrier material can vary within wide limits. For example, carrier materials which have an inner surface area of about 50–300 $m^2/g$ and especially about 100–200 $m^2/g$ (measured according to BET) are suitable.

Examples of carrier materials which can be used include silica, aluminum oxide, aluminum silicates or spinels. Silica is the preferred carrier material.

In accordance with the method of this invention, the catalyst carrier first is impregnated with an aqueous solution containing a water-soluble palladium compound and a first amount of a water-soluble gold compound. Separate solutions of the palladium and gold compounds also can be used successively, but it is less convenient to proceed in that fashion. Palladium (II) chloride, sodium palladium (II) chloride, palladium (II) nitrate or palladium (II) sulfate are examples of suitable water-soluble palladium compounds, whereas auric (III) chloride or activity (III) acid can be used as the water-soluble gold compounds. Activity (III) acid and sodium palladium (II) chloride are preferred because of their good water solubility. The volume of solution used for impregnating the carrier with the precious metals is important. For effective deposition, the volume of the impregnating solution preferably is from about 95 to about 100% of the absorptive capacity of the catalyst carrier and preferably it is about 98–99%. Such impregnation technique is characterized as the "incipient wetness" method.

After impregnation of the carrier with the water-soluble palladium and the first amount of the water-soluble gold compounds, the water-soluble palladium and the water-soluble gold compounds are fixed to the carrier as water-insoluble palladium and gold compounds. The fixing solution is one which comprises an alkaline solution, for example, an aqueous solution which contains alkali metal hydroxides, alkali metal bicarbonates and/or alkali metal carbonates. It is particularly preferred to use aqueous solutions of sodium hydroxide or potassium hydroxide. The amount of alkaline compound employed is such that the ratio of alkaline metal to anion from the water-soluble precious metal compounds is from about 1:1 to about 2:1, preferably from about 1.2:1 to about 1.8:1. By treatment with the alkaline solution, the precious metal water-soluble compounds are converted to water-insoluble compounds believed to be hydroxides and/or oxides, at least in the case where the alkaline solution is a solution of sodium hydroxide or potassium hydroxide.

Preferably, the carrier is impregnated in the first gold fixing stage by a process designated "rotation immersion" which is set forth in U.S. Pat. No. 5,332,710 issued Jul. 26, 1994 to Nicolau et al. the entire disclosure of which is hereby incorporated herein in its entirety by reference. In this process, the fixed carriers are immersed in the alkaline fixing solution and tumbled or rotated therein during the initial stages of the precipitation of the water-insoluble precious metal compounds. The rotation or tumbling of the carrier in the alkaline fixing solution preferably proceeds for at least about 0.5 hour upon the initial treatment and, most preferably, for at least about 2.5 hours. The rotation immersion treatment can last as long as up to about 4 hours before the treated carriers are allowed to stand in the fixing solution to insure that complete precipitation of the precious metal compounds takes place.

Any type of rotation or tumbling equipment can be used as the exact apparatus utilized is not critical. What is critical, however is the extent of the rotating motion. Thus, the rotation preferably is sufficient such that all surfaces of the impregnated carriers are evenly contacted with the alkaline fixing solution. The rotation preferably is not harsh enough such that actual abrasion of the water-insoluble precious metal compounds takes place such that the water-insoluble compounds are abraded off the carriers surface. On the other hand, it has been found or believed that some small extent of abrasion of the water-insoluble precious metal compounds actually works to more evenly distribute the water-insoluble precious metal compounds on the carrier surface. The extent of rotation preferably is about 1 to about 10 rpm and possibly even higher depending upon the exact carrier utilized and the amount of precious metal to be deposited on the carrier. The rpm to be used is variable and can also depend upon the apparatus utilized, the size and shape of the carrier, the type of carrier, metal loadings, etc., but preferably falls within the guidelines expressed above that while a small amount of abrasion can be beneficial, it is not to be such that the water-insoluble compounds are actually abraded off the carrier surface.

Another method of fixing the precious metals onto the carrier is the "incipient wetness" method whereby as above described, a specified volume of the fixing solution, e.g., aqueous alkali metal hydroxide, equal to the dry absorbtivity of the carrier is poured onto the porous supports which have been impregnated with the water-soluble precious metal compounds. The treated carriers are allowed to stand until precipitation is complete. When fixing is performed by the incipient wetness method, the impregnated carriers are air dried prior to fixing with the aqueous metal hydroxide.

Alternatively, the fixing step can be divided into at least two separate stages of treatment with the alkaline fixing solution. Such a process is described in U.S. Pat. No. 5,314,858, issued May 24, 1994 to Colling the entire disclosure of which is hereby incorporated herein in its entirety by reference. In each separate fixing treatment, the amount of the alkaline reactive compound is no more than that equal to the molar amount required to react with all of the precious metal compound which is present on the carrier as a water soluble compound. No excess of reactive compound is used. Preferably, the amount of reactive compound used in each fixing stage is less than the molar amount required to react with all of the water soluble precious metal compound. Each fixing stage is conducted by impregnating the dried impregnated carrier with the alkaline fixing solution in an amount equal to about the dry absorbtivity of the carrier. The amount of the alkaline compound contained in solution preferably is such that the ratio of alkali metal to anion from the water soluble precious metal compounds be from about 0.7 to 1:1 molar in the first stage and from about 0.2 to 0.9:1 molar in the second stage. Preferably, the total amount of alkali metal to anion ranges from about 1.2 to about 1.6:1 molar for the whole fixing step. Subsequent to treatment in the first fixing stage, the treated carriers are allowed to stand for a sufficient period of time to allow precipitation of the water-insoluble precious metal compounds. The period of time can vary but typically ranges from about 2 hours to about 8 hours before the carrier is treated again with the second portion of alkaline fixing solution. Subsequent to treatment in the second fixing stage, the treated carriers are allowed to stand again for at least an additional 2 hours, preferably, at least about 4 hours and can stand to complete precipitation for up to about 16 hours.

The treatment in the second fixing stage can be equivalent to that of the first stage wherein the treated and partially fixed carriers are impregnated with the fixing solution at the desired alkaline concentration and in a total volume solution again equivalent to the dry absorbtivity of the carrier. Alternatively, the carrier can be impregnated in the second fixing stage by a process designated "rotation immersion" as discussed above. In this process, the once-fixed carriers are immersed in the alkaline fixing solution and tumbled or rotated therein during the initial stages of the precipitation of the water-insoluble precious metal compounds as discussed earlier.

After the first amount of water-soluble gold has been fixed, a second amount of gold can be impregnated and fixed according to the same methods described above for impregnating and fixing the first amount of gold to the carrier. Thus, any of the gold salts described above for use in the first stage gold addition can be used to add the second amount of gold. Likewise, any of the fixing methods, such as "rotation immersion", incipient wetness and double fixing methods as described previously can be used to precipitate the insoluble gold compound onto the carrier. Preferably, the second amount of gold is fixed to the carrier by the "incipient wetness" method by impregnating the carrier with a solution of the second amount of the water-soluble gold compound and an aqueous alkaline fixing agent or by treating the carrier impregnated with the second amount of water-soluble gold compound with an aqueous alkaline fixing solution, and allowing the impregnated carrier to stand for up to about 16 hours or more to allow precipitation of the water-insoluble gold compounds. The volume of fixing solution is that equal to the dry absorbtivity of the carrier and the amount of alkaline compound used is in excess on a molar basis that is required to react with all of the impregnated water-soluble gold compounds.

Subsequent to fixing the precious metal compounds to the carrier, the carrier is washed with deionized water to remove anions, such as chloride ions, which are still contained on the carrier and freed from the impregnating solutions. Washing is continued until all of the anions are removed from the carrier. To ensure substantially complete removal of the anions, such as chloride ion from the catalyst, the wash effluent is tested with silver nitrate until the silver nitrate test is negative, i.e., no silver chloride formation. After washing the ions from the catalyst, the catalyst then is dried at temperatures not to exceed about 150° C. under an inert atmosphere such as a continuous nitrogen flow. Washing and drying can be performed after the palladium and first amount of gold have been fixed to the carrier and again after the second amount of gold has been added and fixed or washing and drying can be performed once all the precious metals been fixed to the carrier, i.e., subsequent to fixing the second amount of gold.

The fixed material then is treated with a reducing agent to convert the precious metal salts and compounds which are present into metallic form. The reduction can be carried out in the liquid phase, for example, with aqueous hydrazine hydrate, or, preferably, in the gas phase, such as, with hydrogen or hydrocarbons, for example, ethylene. If the reduction is carried out with a solution of hydrazine hydrate, the reaction is preferably carried out at normal temperature. When the reduction is carried out in the gas phase, it can be advantageous to carry out the reaction at an elevated temperature, for example, at about 100°–200° C. in the case of reduction with ethylene. The reducing agent is appropriately employed in excess to be certain that all of the precious metal salts and compounds are converted into the metallic form. When hydrazine is employed, the weight ratio of hydrazine to precious metals ranges from about 10:1 to about 15:1, preferably, about 12:1. After reducing the palladium and gold water-insoluble compounds, the carrier is dried in an inert atmosphere at about 150° C. As with the washing and drying steps, reduction of the precious metals can be done after each fixing step or reduction can be done after all the precious metals have been fixed to the carrier. Moreover, reduction can take place either before or after the catalysts are washed to remove anionic materials.

The relative amount of water-soluble gold compound added in each impregnation step is not critical. From about ½ to about ¾ of the total gold on the final catalyst is added during the first impregnation step, with the balance added in the second impregnation step. Preferably, the quantity of palladium and gold compounds employed is such as to provide about 3 to about 8 grams of palladium and about 1.5 to about 14 grams of gold per liter of finished catalyst. Catalysts containing higher or lower amounts of the precious metals relative to that recited above can be useful in the formation of vinyl acetate by reaction of ethylene, oxygen and acetic acid in the vapor phase as long as the catalyst is formed by the novel method set forth herein. Thus, the ratio of gold/palladium in the finished catalyst can range from about 0.2:1 to about 2:1, preferably, from about 0.4:1 to about 1.5:1.

Depending on the use for which the catalyst prepared in this way is intended, the catalyst also can be provided with customary additives. Thus, for example, additions of alkali metal acetates are advantageous when the catalyst is to be used for the preparation of unsaturated esters from olefins, oxygen and organic acids. In this case, for example, the catalyst can be impregnated with an aqueous solution of potassium acetate, sodium acetate, lithium acetate, rubidium acetate or cesium acetate and then washed and dried.

The catalysts according to the present invention can be used with particular advantage in the preparation of vinyl acetate from ethylene, oxygen and acetic acid in the gas phase. For this purpose, those catalysts according to the present invention which contain silica as the support material and additives of alkali metal acetates are particularly suitable. In the preparation of vinyl acetate, such catalysts are also distinguished by high activity and selectivity for vinyl acetate and by long life.

When vinyl acetate is prepared using a catalyst prepared according to the present invention, a stream of gas, which contains ethylene, oxygen or air and acetic acid is passed over the catalyst. The composition of the stream of gas can be varied within wide limits, taking into account the explosive limits. For example, the molar ratio of ethylene to oxygen can be about 80:20 to about 98:2 and the molar ratio of acetic acid to ethylene can be about 100:1 to about 1:100 and the content of gaseous alkali metal acetate can be about 2–200 ppm, relative to the acetic acid employed. The stream of gas also can contain other inert gases, such as nitrogen, carbon dioxide and/or saturated hydrocarbons. Reaction temperatures which can be used are elevated temperatures, preferably those in the range of about 100°–250° C., preferably, 130°–200° C. The pressure employed can be a somewhat reduced pressure, normal pressure or elevated pressure, preferably a pressure of up to about 20 atmospheres gauge.

Catalysts of the present invention employed to prepare vinyl acetate show an improved space time yield, a reduced carbon dioxide and ethyl acetate selectivity as well as reduced heavy ends.

The following examples are intended to further illustrate the present invention and are not intended to limit the scope of the present invention.

EXAMPLES I, II and III

The catalysts were prepared on spherical silica carriers provided by Sud Chemie with diameters of about 5 mm. The carriers were divided into three batches (Examples I, II and III) of 250 cc each. The catalysts in Example I were prepared according to the standard method (described below). The catalysts in Example II were prepared according to the same method as the catalysts in Example I except that an additional amount of gold was added to the catalysts. The amount of gold was about equal to the amount of palladium added to the catalysts. The catalysts of Example III contained the same amounts of palladium and gold as Example II but were prepared according to the two step gold addition method of the present application.

All the carriers were impregnated with an aqueous solution containing sodium palladium tetrachlorate and sodium tetrachloroaurate. The volume of solution employed was equivalent to the amount of solution that the carriers were capable of absorbing (incipient wetness method). In Example I, the carriers were impregnated with a sufficient amount of palladium and gold water-soluble salts such that the resulting catalysts would have about 7 gm/l of palladium metal and about 4 gm/l of gold metal. In Examples II and III, the carriers were impregnated with a sufficient amount of palladium and gold water soluble salts such that each catalyst would have about 7 gm/l of palladium metal and about 7 gm/l of gold metal. In Example III, 4 gm/l of gold was added during the first impregnation.

After impregnation, the carriers were placed in a rotoevaporator (without vacuum) and treated with 283 cc of a 50% w/w aqueous solution of sodium hydroxide to fix the water-soluble salts of palladium and gold to the carriers as water-insoluble hydroxide compounds of palladium and gold. The amount of sodium hydroxide used was about 120% of the stoichiometric equivalent needed to convert the metal salts to their metal hydroxides. The carriers were immediately rotated at about 5 rpm for about 2.5 hours. The temperature of the sodium hydroxide solution was maintained during roto-immersion at about 70° C. by rotating in a hot water bath.

The fixed carriers were drained and placed in 500 ml graduated cylinders with dip tubes and washed for 5 hours with deionized water until the effluent from the wash tested negative with silver nitrate, i.e., no silver chloride formation. The washed carriers were then placed in 500 ml round bottom flasks and placed in an oven under a continuous flow of nitrogen to dry overnight, i.e., about 16 hours. The oven temperature was maintained at about 150° C.

The water-insoluble palladium and gold compounds on the dried carriers then were reduced to palladium and gold metal by the vapor phase method to form the catalysts. A blend of 5% ethylene in nitrogen was passed over the carriers in the oven for about 5 hours at a temperature of about 150 degrees C. The flow rate of the gas blend was about 0.5 SCFH at atmospheric pressure. After reduction, the catalysts were removed from the oven and allowed to cool to room temperature.

The catalysts in Examples I and II were impregnated with an aqueous solution of about 10 gm of potassium acetate (concentra-tion about 40 gm/l) by the incipient wetness method, and dried in a fluid bed dryer for about 1 hour at about 150° C.

Subsequent to reduction in ethylene as described above, the catalysts from Example III were further impregnated with a solution of sodium tetrachloroaurate and 1.65 gm of a 50% w/w aqueous sodium hydroxide fixing solution such that the catalysts would have an additional 3 gm/l of gold for a total of about 7 gm/l of gold on the finished catalysts. The amount of sodium hydroxide used corresponded to about 180% of the stoichiometric equivalents needed to convert the gold salts to gold metal. The catalysts were allowed to sit in the solution overnight, i.e., about 16 hours. The catalysts were then placed in a 500 ml graduated cylinder with a dip tube and washed for 5 hours with deionized water until the effluent from the wash tested negative with silver nitrate.

The washed catalysts were placed in a 500 ml round bottom flask in an oven at about 150° C. under a continuous nitrogen flow overnight. A blend of 5% ethylene in nitrogen was passed over the washed and dried catalysts for about 5 hours at about 150° C. to reduce the gold salts to gold metal.

After the catalysts were cooled to room temperature, the catalysts were impregnated with an aqueous solution of 10 gm of potassium acetate(concentration about 40 gm/l). The catalysts were allowed to stand for about 15 min. then dried in a fluid bed dryer at about 100° C. for about 1 hour.

A 30 cc. sample of the catalyst was placed in a plug flow, tubular reactor, 3 ft. in length and with an I. D. of 0.75 in. The tube was equipped with an 0.125 in. concentric thermocouple. Acetic acid, ethylene, oxygen, and nitrogen are passed through the tube at a temperature such that about 45 percent of the oxygen was converted to a product. The products were analyzed off-line by vapor phase chromatography.

Results of the product analysis are disclosed in Table 1. The results show that catalysts prepared according to the two step gold method show a lowered carbon dioxide selectivity of 5.4%, a lowered ethyl acetate selectivity of 0.08% and an increased STY of 611 in contrast to the higher carbon dioxide and ethyl acetate selectivities and the lower STY of the catalysts prepared by the standard procedure. Additionally, the catalysts prepared by the two step gold addition method had a reduced heavy ends selectivity of 0.97% in contrast to heavy ends of 1.26% by the catalysts prepared by the standard method with the same amount of gold as the catalysts made by the two step method. Thus, the two step gold addition method of the present application provides for improved vinyl acetate catalysts.

About 60 ml of each type of catalyst prepared as described above were placed in separate chrome-nickel steel baskets. The temperature of each basket was measured by a thermocouple at both the top and the bottom of each basket. Each reaction basket was placed in a Berty reactor and was maintained at a temperature which provided about 45% oxygen conversion with an electric heating mantle. A gas mixture of about 50 normal liters (measured at N.T.P.) of ethylene, about 10 normal liters of oxygen, about 49 normal liters of nitrogen and about 50 gm of acetic acid was caused to travel under pressure at about 12 atmospheres through each basket. Analysis of the products was accomplished by on-line gas chromatographie analysis combined with off-line liquid product analysis by condensing the product stream at about 10° C. to obtain optimum analysis of the end products.

The results of the tests are shown in Table 2. The tests show a distinct lessening of the selectivity to the manufacture of by-products carbon dioxide and ethyl acetate, 9.9 vs. 10.6 for carbon dioxide selectivity and 0.042 vs. 0.048 for ethyl acetate selectivity when compared in this test to the same catalyst when manufactured by the prior art method. The amount of heavy ends manufacture was not affected, and the activity of the catalyst was only marginally affected by the use of the catalyst of the present invention.

TABLE 1

| CATALYST | G/L PD | G/L AU | % SELECTIVITY $CO_2$ | ETHYL ACETATE | HEAVY ENDS | ACTIVITY |
|---|---|---|---|---|---|---|
| Example I | 7 | 7 | 10.6 | 0.048 | 1.57 | 2.39 |
| Example II | 7 | 7 | 9.9 | 0.042 | 1.58 | 2.34 |

TABLE 2

| CATALYST | G/L PD | G/L AU | % SELECTIVITY $CO_2$ | ETHYL ACETATE | HEAVY ENDS | STY G/L/HR | % O2 CONVERSION | REACTION TEMP °C. |
|---|---|---|---|---|---|---|---|---|
| Examples I | 7 | 4 | 5.8 | 0.13 | 0.93 | 606 | 45.2 | 141 |
| Examples II | 7 | 7 | 5.7 | 0.12 | 1.26 | 573 | 45.2 | 133 |
| Examples III | 7 | 7 | 5.4 | 0.08 | 0.97 | 611 | 45.1 | 137 |

What is claimed:

1. In a process for preparing a catalyst for synthesizing unsaturated esters, wherein a catalyst carrier is impregnated with a water soluble palladium compound and a water soluble gold compound, fixing the water soluble palladium compound and the water soluble gold compound to the carrier as a water insoluble palladium compound and a water insoluble gold compound and reducing the water insoluble palladium compound to palladium metal and the water insoluble gold compound to gold metal, the improvement comprising impregnating and fixing the water soluble gold compound in two steps, wherein a first amount of the water soluble gold compound is impregnated on the carrier and then fixed to the carrier as a first amount of the water insoluble gold compound followed by impregnating the carrier with a second amount consisting essentially of the water soluble gold compound and fixing the second amount of the water soluble gold compound as a second amount of the water insoluble gold compound.

2. The method of claim 1, wherein the water-soluble palladium compound is fixed to the catalyst carrier prior to impregnating and fixing the catalyst carrier with the first amount of water-soluble gold compound.

3. The method of claim 1, wherein the water-soluble palladium compound and the first mount of water-soluble gold compound are impregnated then fixed on the catalyst carrier simultaneously.

4. The method of claim 1, wherein the water-insoluble palladium compound and the first and second amount of water-insoluble gold compound are reduced to the palladium and gold metal simultaneously.

5. The method of claim 2, wherein the fixed palladium compound and the first amount of the fixed water-soluble gold compound are reduced prior to impregnating the catalyst carrier with the second amount of water-soluble gold compound.

6. The method of claim 1, wherein the water-soluble palladium compound is fixed by immersing the carrier impregnated with the water-soluble palladium compound in a solution containing a compound reactive with the water-soluble palladium compound for about 16 hours to precipitate a water-insoluble palladium compound on the impregnated carrier.

7. The method of claim 1, wherein the water-soluble palladium impregnated carrier is rotated in a solution containing a compound reactive with the water-soluble palladium compound to complete precipitation of the water-soluble palladium compound to a water-insoluble palladium compound.

8. The method of claim 7, wherein the impregnated carrier is rotated from about 1 to about 10 rpm for at least about 0.5 hour.

9. The method of claim 1, wherein the first amount of water-soluble gold compound impregnated carrier is rotated in a solution containing a compound reactive with the water-soluble gold compound to complete precipitation of the water-insoluble gold compound.

10. The method of claim 9, wherein the impregnated carrier is rotated from about 1 to about 10 rpm for at least about 0.5 hour.

11. The method of claim 1, wherein the carrier comprising the second amount of impregnated water-soluble gold compound is rotated to complete precipitation of the water-insoluble gold compound.

12. The method of claim 11, wherein the carrier is rotated from about 1 to about 10 rpm for at least about 0.5 hour.

13. The method of claim 1, wherein the first amount of the water-soluble gold compound impregnated on the carrier is fixed by immersing the impregnated carrier in a solution containing a compound reactive with the first amount of the water-soluble gold compound for about 16 hours to precipitate a water-insoluble gold compound of the first amount of the water-soluble gold compound.

14. The method of claim 1, wherein the second amount of the water-soluble gold compound impregnated on the carrier is fixed by immersing the impregnated carrier in a solution containing a compound reactive with the second amount of water-soluble gold compound for about 16 hours to precipitate a water-insoluble gold compound from the second amount of water-soluble gold compound.

15. The method of claim 1, wherein the carrier is impregnated with a solution containing the second amount of the water-soluble gold compound and a fixing compound.

16. The method of claim 1, wherein the water-insoluble palladium compound and the first and second amount of the water-insoluble gold compound are reduced to palladium metal and to gold metal with a reducing agent comprising ethylene or hydrazine.

17. The method of claim 16, wherein the reducing agent is hydrazine and a weight ratio of hydrazine to the palladium and the gold metals is about 12:1.

18. The method of claim 1, wherein the water-insoluble palladium compound and the first amount of the water-insoluble gold compound are fixed in two stages, a first fixing stage with a solution containing a compound reactive with the water-soluble palladium compound and reactive with the first amount of water-soluble gold compound to precipitate the water-insoluble palladium compound and the first amount of the water-insoluble gold compound on the carrier, then contacting the carrier with an additional solution containing a compound reactive with the water-soluble palladium and gold compounds in a second fixing step to further precipitate water-insoluble palladium and gold compounds on the carrier.

19. The method of claim 1, further comprising impregnating the carrier with an alkali metal acetate.

20. The method of claim 19, wherein the alkali metal acetate comprises potassium acetate sodium acetate, lithium acetate, rubidium acetate or cesium acetate.

21. The method of claim 1, further comprising washing and drying the carrier after each fixing step.

22. The method of claim 1, wherein the water-soluble palladium compounds comprise palladium chloride, sodium palladium chloride or palladium nitrate.

23. The method of claim 1, wherein the water soluble gold compounds comprise auric chloride or cloroauric acid.

24. The method of claim 1, wherein the water-soluble palladium compound and the first amount of the water-soluble gold compound are fixed to the carrier in a fixing solution comprising sodium ions wherein the weight ratio of the sodium ions to any chloride ions from the water-soluble palladium compound and the first amount of the water-soluble gold compound is about 1.2:1.

25. The method of claim 1, wherein the second water-soluble gold compound is fixed to the carrier in a fixing solution comprising sodium ions wherein the weight ratio of the sodium ions to any chloride ions from the second amount of the water-soluble gold compound is about 1.8:1.

26. The method of claim 1, wherein the amount of palladium metal on the carrier of the catalyst comprises a concentration of about 3 gm/l to about 8 gm/l and the amount of gold metal on the carrier of the catalyst comprises a concentration of from about 1.5 gm/l to about 14 gm/l.

27. The method of claim 1, wherein the amount of palladium metal on the catalyst comprises about 7 gm/l and the amount of gold metal on the catalyst comprises about 7 gm/l.

28. The method of claim 1, wherein the catalyst has a gold/palladium weight ratio of from about 0.2:1 to about 2:1.

29. The method of claim 1, wherein from about ½ to about ¾ of the total gold on the catalyst is added during the first impregnation step and the balance is added in the second impregnation step.

* * * * *